(12) United States Patent
Difiore et al.

(10) Patent No.: US 8,920,404 B2
(45) Date of Patent: Dec. 30, 2014

(54) REDUCTION OF RECIRCULATION IN CATHETERS

(75) Inventors: Attilio E. Difiore, Taylorsville, UT (US); Daniel J. Triplett, Providence, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 111 days.

(21) Appl. No.: 13/329,166

(22) Filed: Dec. 16, 2011

(65) Prior Publication Data

US 2012/0089115 A1    Apr. 12, 2012

Related U.S. Application Data

(62) Division of application No. 10/883,934, filed on Jul. 2, 2004, now abandoned.

(51) Int. Cl.
*A61M 25/00* (2006.01)

(52) U.S. Cl.
CPC ........ *A61M 25/0068* (2013.01); *A61M 25/0071* (2013.01); *A61M 2025/0073* (2013.01); *A61M 2206/14* (2013.01)
USPC ............................ 604/523; 604/264; 604/6.16

(58) Field of Classification Search
CPC ............ A61M 1/0058; A61M 25/007; A61M 3/0279; A61M 2025/0031; A61M 3/0283; A61M 25/0068; A61M 1/285; A61M 2025/0037; A61M 25/0032; A61M 2025/0073; A61M 2025/0036; A61M 2025/004; A61M 25/0029; A61M 25/0071; A61M 25/0023; A61M 2025/0035; A61M 2025/0039
USPC ................. 604/27, 30, 43, 6.06, 6.16, 29, 35, 604/93.01, 264, 523–532, 544
See application file for complete search history.

(56) References Cited

U.S. PATENT DOCUMENTS

| | | |
|---|---|---|
| 1,696,018 A | 12/1928 | Scheliberg |
| 2,393,002 A | 1/1946 | Smith |
| 3,256,885 A | 6/1966 | Higgins et al. |

(Continued)

FOREIGN PATENT DOCUMENTS

| | | |
|---|---|---|
| CA | 1150122 | 7/1983 |
| DE | 8815869 U1 | 2/1989 |

(Continued)

OTHER PUBLICATIONS

Bard Access Systems, Soft-Cell Dual Lumen Catheter, Instructions for Soft-Cell Straight and Precurved (PC) Catheters, 1999.

(Continued)

*Primary Examiner* — Aarti B Berdichevsky
*Assistant Examiner* — Laura Schell
(74) *Attorney, Agent, or Firm* — Rutan & Tucker, LLP (57) ABSTRACT

A catheter tip designed to reduce the outflow velocity and/or directional momentum of fluid being infused by a catheter having such a tip. In one variation, a plurality of channels is provided at the distal portion of the catheter to increase the outflow cross-sectional area. In another variation, the diameter of the catheter at its distal portion where the fluid exits is increased. In yet another variation, a bullet-shaped nose is implemented which may decrease turbulence at the distal end of catheter tip. The low velocity outflow catheter tip may also be implemented on a dual lumen catheter, such as a hemodialysis catheter, to reduce recirculation rate. Various device configurations and methods for such implementations are also disclosed.

10 Claims, 4 Drawing Sheets

(56) References Cited

U.S. PATENT DOCUMENTS

| | | | |
|---|---|---|---|
| 3,416,532 A | 12/1968 | Grossman | |
| 3,426,759 A | 2/1969 | Smith | |
| 3,812,851 A | 5/1974 | Rodriguez | |
| 3,929,126 A | 12/1975 | Corsaut | |
| 4,129,129 A | 12/1978 | Amrine | |
| 4,149,535 A | 4/1979 | Volder et al. | |
| 4,385,631 A | 5/1983 | Uthmann et al. | |
| 4,451,252 A | 5/1984 | Martin et al. | |
| 4,493,696 A | 1/1985 | Uldall et al. | |
| 4,557,261 A | 12/1985 | Rugheimer et al. | |
| 4,563,170 A * | 1/1986 | Aigner | 604/6.06 |
| 4,563,180 A | 1/1986 | Jervis et al. | |
| 4,581,017 A | 4/1986 | Sahota | |
| 4,583,986 A | 4/1986 | Lapidus | |
| 4,626,240 A | 12/1986 | Edelman et al. | |
| 4,643,711 A | 2/1987 | Bates | |
| 4,666,426 A | 5/1987 | Aigner et al. | |
| 4,681,564 A | 7/1987 | Landreneau | |
| 4,681,570 A | 7/1987 | Dalton | |
| 4,682,978 A | 7/1987 | Martin et al. | |
| 4,687,471 A | 8/1987 | Twardowski et al. | |
| 4,755,176 A | 7/1988 | Patel | |
| 4,769,006 A | 9/1988 | Papantonakos et al. | |
| 4,772,269 A | 9/1988 | Twardowski et al. | |
| 4,808,155 A | 2/1989 | Mahurkar | |
| 4,842,582 A | 6/1989 | Mahurkar | |
| 4,863,441 A | 9/1989 | Lindsay et al. | |
| 4,867,742 A | 9/1989 | Calderon | |
| 4,895,561 A | 1/1990 | Mahurkar | |
| 4,935,044 A | 6/1990 | Schoenpflug et al. | |
| 4,961,809 A | 10/1990 | Martin et al. | |
| 4,970,926 A | 11/1990 | Ghajar et al. | |
| 4,981,477 A | 1/1991 | Schon et al. | |
| 4,985,014 A | 1/1991 | Orejola | |
| 5,015,230 A | 5/1991 | Martin et al. | |
| 5,041,107 A | 8/1991 | Heil, Jr. | |
| 5,053,004 A | 10/1991 | Markel et al. | |
| 5,053,023 A | 10/1991 | Martin | |
| 5,057,073 A | 10/1991 | Martin | |
| 5,106,376 A | 4/1992 | Mononen et al. | |
| 5,135,599 A | 8/1992 | Martin et al. | |
| 5,156,592 A | 10/1992 | Martin et al. | |
| 5,167,623 A | 12/1992 | Cianci et al. | |
| 5,171,216 A | 12/1992 | Dasse et al. | |
| 5,171,227 A | 12/1992 | Twardowski et al. | |
| 5,188,593 A | 2/1993 | Martin | |
| 5,195,962 A | 3/1993 | Martin et al. | |
| 5,209,723 A | 5/1993 | Twardowski et al. | |
| 5,221,255 A | 6/1993 | Mahurkar et al. | |
| 5,221,256 A | 6/1993 | Mahurkar | |
| 5,226,880 A | 7/1993 | Martin et al. | |
| 5,242,398 A | 9/1993 | Knoll et al. | |
| 5,324,274 A | 6/1994 | Martin | |
| 5,342,295 A | 8/1994 | Imran | |
| 5,346,471 A | 9/1994 | Raulerson | |
| 5,348,536 A | 9/1994 | Young et al. | |
| 5,350,358 A | 9/1994 | Martin | |
| 5,374,245 A | 12/1994 | Mahurkar | |
| 5,378,230 A | 1/1995 | Mahurkar | |
| 5,395,316 A | 3/1995 | Martin et al. | |
| 5,405,320 A | 4/1995 | Twardowski et al. | |
| 5,405,341 A | 4/1995 | Martin | |
| 5,451,233 A | 9/1995 | Yock | |
| 5,472,417 A | 12/1995 | Martin et al. | |
| 5,472,432 A | 12/1995 | Martin | |
| 5,505,710 A | 4/1996 | Dorsey, III | |
| 5,509,897 A | 4/1996 | Twardowski et al. | |
| 5,569,182 A | 10/1996 | Twardowski et al. | |
| 5,571,093 A | 11/1996 | Cruz et al. | |
| 5,607,462 A | 3/1997 | Imran | |
| 5,616,137 A | 4/1997 | Lindsay | |
| 5,624,392 A | 4/1997 | Saab | |
| 5,643,226 A | 7/1997 | Cosgrove et al. | |
| 5,665,067 A | 9/1997 | Linder et al. | |
| 5,685,865 A | 11/1997 | Cosgrove et al. | |
| 5,685,867 A | 11/1997 | Twardowski et al. | |
| 5,693,030 A | 12/1997 | Lee et al. | |
| 5,718,678 A | 2/1998 | Fleming, III | |
| 5,718,692 A | 2/1998 | Schon et al. | |
| 5,738,649 A | 4/1998 | Macoviak | |
| 5,769,828 A | 6/1998 | Jonkman | |
| 5,776,111 A | 7/1998 | Tesio | |
| 5,792,094 A | 8/1998 | Stevens et al. | |
| 5,797,869 A | 8/1998 | Martin et al. | |
| 5,800,384 A | 9/1998 | Russell et al. | |
| 5,800,414 A | 9/1998 | Cazal et al. | |
| 5,807,311 A | 9/1998 | Palestrant | |
| 5,807,318 A | 9/1998 | St. Goar et al. | |
| 5,810,789 A | 9/1998 | Powers et al. | |
| 5,814,016 A | 9/1998 | Valley et al. | |
| 5,858,019 A | 1/1999 | Ashraf | |
| 5,947,953 A | 9/1999 | Ash et al. | |
| 5,961,486 A | 10/1999 | Twardowski et al. | |
| 5,971,968 A | 10/1999 | Tu et al. | |
| 5,976,103 A | 11/1999 | Martin | |
| 5,984,908 A | 11/1999 | Davis et al. | |
| 5,989,206 A | 11/1999 | Prosl et al. | |
| 6,001,079 A | 12/1999 | Pourchez | |
| 6,126,631 A | 10/2000 | Loggie | |
| 6,156,016 A | 12/2000 | Maginot | |
| 6,161,547 A | 12/2000 | Barbut | |
| 6,171,275 B1 | 1/2001 | Webster, Jr. | |
| 6,190,349 B1 | 2/2001 | Ash et al. | |
| 6,206,849 B1 | 3/2001 | Martin et al. | |
| 6,217,527 B1 | 4/2001 | Selmon et al. | |
| 6,280,423 B1 | 8/2001 | Davey et al. | |
| 6,293,927 B1 | 9/2001 | McGuckin, Jr. | |
| 6,387,087 B1 | 5/2002 | Grooters | |
| 6,443,922 B1 | 9/2002 | Roberts et al. | |
| 6,540,714 B1 | 4/2003 | Quinn | |
| 6,582,409 B1 | 6/2003 | Squitieri | |
| 6,620,118 B1 | 9/2003 | Prosl et al. | |
| 6,638,242 B2 | 10/2003 | Wilson et al. | |
| 6,682,519 B1 | 1/2004 | Schon | |
| 6,695,832 B2 | 2/2004 | Schon et al. | |
| 6,712,797 B1 | 3/2004 | Southern, Jr. | |
| 6,723,084 B1 | 4/2004 | Maginot et al. | |
| 6,814,718 B2 | 11/2004 | McGuckin, Jr. et al. | |
| 6,858,019 B2 | 2/2005 | McGuckin, Jr. et al. | |
| 6,999,809 B2 | 2/2006 | Currier et al. | |
| 2002/0087108 A1 | 7/2002 | Maginot et al. | |
| 2002/0091362 A1 | 7/2002 | Maginot et al. | |
| 2002/0099327 A1 | 7/2002 | Wilson et al. | |
| 2002/0107506 A1 * | 8/2002 | McGuckin et al. | 604/523 |
| 2002/0188167 A1 | 12/2002 | Viole et al. | |
| 2003/0032918 A1 * | 2/2003 | Quinn | 604/43 |
| 2003/0088213 A1 | 5/2003 | Schweikert et al. | |
| 2003/0149395 A1 | 8/2003 | Zawacki | |
| 2003/0153898 A1 | 8/2003 | Schon et al. | |
| 2003/0187411 A1 | 10/2003 | Constantz | |
| 2004/0054321 A1 | 3/2004 | Schon et al. | |
| 2004/0059314 A1 | 3/2004 | Schon et al. | |
| 2004/0065333 A1 | 4/2004 | Wilson et al. | |
| 2004/0075198 A1 | 4/2004 | Schweikert et al. | |
| 2004/0254562 A1 * | 12/2004 | Tanghoj et al. | 604/523 |
| 2004/0267106 A1 * | 12/2004 | Segner et al. | 600/374 |
| 2006/0004316 A1 | 1/2006 | Difiore et al. | |

FOREIGN PATENT DOCUMENTS

| | | |
|---|---|---|
| EP | 0132344 A2 | 1/1985 |
| EP | 0495263 A1 | 7/1992 |
| EP | 0711574 A1 | 5/1996 |
| WO | 9717102 | 5/1997 |
| WO | 0258776 A2 | 8/2002 |
| WO | 03030960 A2 | 4/2003 |
| WO | 03033049 A2 | 4/2003 |

OTHER PUBLICATIONS

Davenport, Andrew; Mehta, Sangeeta, ADQI, Acute Dialysis Quality Initiative, Workgroup 6, Access and Anti-Coagulation, pp. 1-24, Accessed on Oct. 26, 2003.

(56) References Cited

OTHER PUBLICATIONS

Hemodialysis Catheter, Multidisciplinary Engineering Solutions, pp. 1-2, 2003.
Placement of Hemodialysis Catheters, University of Virginia Health Systems, Oct. 26, 2003, pp. 1-4.
Twardowski, Zbylut J.; Moore, Harold L., Side Holes at the Tip of Chronic Hemodialysis Catheters are Harmful, The Journal of Vascular Access 2001; 2:8-16, University of Missouri, Dialysis Clinic Incorporated, Columbia, Missouri USA.
U.S. Appl. No. 10/883,934, filed Jul. 2, 2004 Advisory Action dated May 10, 2007.
U.S. Appl. No. 10/883,934, filed Jul. 2, 2004, Final Office Action dated Apr. 29, 2009.
U.S. Appl. No. 10/883,934, filed Jul. 2, 2004 Final Office Action dated Mar. 19, 2007.
Davenport, Andrew; Mehta, Sangeeta, ADQI, Acute Dialysis Quality Initiative, Workgroup 6, Access and Anti-Coagulation, pp. 1-24.
Hemodialysis Catheter, Multidisciplinary Engineering Solutions, pp. 1-2.
Information for Patients Hemodialysis Catheter, UC David Medical Group, pp. 1-2.
Kapoian, Toros; Kalifman, Jeffrey L.; Nosher, John; Sherman, Richard A., Dialysis Access and Recirculation, Chapter 5, (14 pages).
Rawn, James D. and Tilney, M.D., Nicholas Tilney, The Hemodialysis Access, Chapter 9, (11 pages).
U.S. Appl. No. 10/883,934, filed Jul. 2, 2004 Final Office Action dated Apr. 29, 2009.
U.S. Appl. No. 10/883,934, filed Jul. 2, 2004 Final Office Action dated Mar. 25, 2010.
U.S. Appl. No. 10/883,934, filed Jul. 2 2004 Non-Final Office Action dated Jul. 31, 2008.
U.S. Appl. No. 10/883,934, filed Jul. 2, 2004 Non-Final Office Action dated May 30, 2007.
U.S. Appl. No. 10/883,934, filed Jul. 2, 2004 Non-Final Office Action dated Nov. 15, 2007.
U.S. Appl. No. 10/883,934, filed Jul. 2, 2004 Non-Final Office Action dated Oct. 1, 2009.
U.S. Appl. No. 10/883,934, filed Jul. 2, 2004 Non-Final Office Action dated Sep. 22, 2006.

* cited by examiner

REDUCTION OF RECIRCULATION IN CATHETERS

CROSS-REFERENCE TO RELATED APPLICATIONS

This application is a division of U.S. patent application Ser. No. 10/883,934, filed Jul. 2, 2004, which is incorporated by reference in its entirety into this application.

BACKGROUND OF THE INVENTION

In various medical situations there is a need to divert blood from the circulatory system and then later reintroduce the removed blood back into the circulatory system. For example, patients with renal problems may require hemodialysis to stay alive. In such a situation, due to the fact that the patient's kidney is not functioning properly to remove biological waste from the patient's circulatory system, the blood must be removed from the patient and treated outside the body to remove the biological wastes, and then returned to the circulatory system. A common approach is to introduce a dual lumen catheter into a blood vessel within the patient's body. The catheter has one lumen for removing blood and another lumen for reintroducing the processed blood back into the patient's circulatory system. The dual lumen catheter allows access to the circulatory system to be established through a single insertion site, and therefore minimize surgical trauma and decrease potential for infection and other complication.

For example, a dual lumen catheter may be inserted into the patient's superior vena cava via the subclavian vein, external jugular vein or the internal jugular vein. A small incision is made to locate the desired vessel for insertion of the catheter. A second incision is made at the desired exit site of the catheter, usually in the area between the nipple and sternal border. A tunneler may then be used to tunnel the distal section of the catheter from the exit site to the vessel entry site. The surgeon locates the desired vein and inserts the distal end of the catheter into it. The surgeon then advances the catheter along the vessel until the distal end of the catheter is inside the superior vena cava. Micropuncture sets, syringes, microinstroducer guidewires, and other surgical tools for catheter placement, which are well known to one of ordinary skill in the art, may be implemented to facilitate the catheter insertion and advancement process. After the catheter is inserted inside the superior vena cava, the position of the distal tip of the venous catheter may then be adjusted. For example, some surgeons prefer to position the distal tip of the catheter just above the right atrium. Once the catheter is put in place, the proximal end of the catheter may then be connected to a hemodialysis machine, which may then extract blood from the patient's body through the catheter, process the blood, and then return the processed blood back into the patient's body through the implanted catheter.

Examples of various catheters for extracting and/or introducing blood into a patients circulatory system are disclosed in U.S. Patent Application, Publication No. 2002/0188167 A1, entitled "MULTILUMEN CATHETER FOR MINIMIZING LIMB ISCHEMIA" published Dec. 12, 2002; U.S. Patent Application, Publication No. 2003/0032918 A1, entitled "CATHETER" published Feb. 13, 2003; U.S. Pat. No. 4,563,180, titled "HIGH FLOW CATHETER FOR INJECTING FLUIDS" issued to Jervis et al., dated Jan. 7, 1986; U.S. Pat. No. 4,863,441, titled "VENOUS RETURN CATHETER" issued to Lindsay et al., dated Sep. 5, 1989; U.S. Pat. No. 5,616,137, titled "LOW VELOCITY AORTIC CANNULA" issued to Lindsay, dated Apr. 1, 1997; U.S. Pat. No. 5,643,226, titled "LOW VELOCITY AORTIC CANNULA" issued to Cosgrove et al., dated Jul. 1, 1997; U.S. Pat. No. 5,685,865, titled "LOW VELOCITY AORTIC CANNULA" issued to Cosgrove et al., dated Nov. 11, 1997; U.S. Pat. No. 5,769,828, titled "TWO-STAGE VENOUS CANNULA WITH EXPANDABLE REINFORCING MEMBER" issued to Jonkman, dated Jun. 23, 2998; U.S. Pat. No. 5,989,206, titled "APPARATUS AND METHOD FOR THE DIALYSIS OF BLOOD" issued to Prosl et al., dated Nov. 23, 1999; U.S. Pat. No. 6,280,423 B1, titled "HIGH FLOW RATE DIALYSIS CATHETERS AND RELATED METHODS" issued to Davey et al., dated Aug. 28, 2001; U.S. Pat. No. 6,387,087 B1, titled "AORTIC CANNULA" issued to Grooters, dated May 14, 2002; U.S. Pat. No. 6,540,714 B1, titled "BLOOD VESSEL CATHETER issued to Quinn, dated Apr. 1, 2003; and U.S. Pat. No. 6,582,409 B1, titled "HEMODIALYSIS AND VASCULAR ACCESS SYSTEMS" issued to Squitieri, dated Jun. 24, 2003; each of which is incorporated herein by reference in its entirety.

Although a dual lumen hemodialysis catheter has various advantages, there may be problems associated with some dual lumen designs, such as recirculation of blood. Because the outflow port(s) and inflow port(s) are both located at the distal section of the catheter, a portion of the processed blood exiting the outflow port may be recaptured by the suction at the inflow port and then processed again. If a large amount of blood is being recirculated and redundantly processed, the efficiency of the hemodialysis process may be significantly decreased. The amount of recirculation may also be affected by turbulence and various fluid dynamics at the distal end of the catheter due to the environment surrounding the distal portion of the catheter.

Therefore, a catheter that is configured to decrease recirculation of blood flow may provide substantial benefits, such as improving the efficiency of the hemodialysis treatment process and decreasing treatment time for the patient. Furthermore, a catheter tip designed to minimize the outflow fluid's impact on the existing flow dynamics of the normal circulatory flow may also be desirable. In addition, a catheter tip having a low fluid outflow profile (e.g., low flow velocity exiting the catheter) may be implemented in various other medical applications where low velocity fluid outflow from a catheter is desired.

BRIEF SUMMARY OF THE INVENTION

Accordingly, described herein is a catheter having a distal tip designed to decrease the outflow velocity of fluid being delivered by the catheter. In one variation, side holes are provided at the distal portion of the catheter to prevent jetting of fluids. In another variation, the distal portion of the catheter, where fluid exits the catheter, has an enlarged cross-sectional area relative to the cross-sectional area of a lumen in the proximal portion of the catheter. In yet another variation, the catheter has a bullet shaped nose at the distal end of the catheter tip. Radially patterned openings may also be provided on the bullet shaped nose to serve as outflow orifice.

The low outflow profile catheter tip may be implemented in a catheter having two or more lumens. For example, a low outflow profile catheter tip may be utilized in a hemodialysis catheter. In one variation, the hemodialysis catheter comprises two lumens where the orifice for each of the lumens at the distal portion of the catheter is staggered along the length of the catheter. The orifice at the distal end of the hemodialysis catheter may be configured with a low outflow profile tip. The low outflow profile tip may decrease the outflow velocity of fluid being infused through the catheter such that the infusion of fluid causes minimal disruption on the existing circulatory flow within the patient's circulatory system. For example, the distal end of the hemodialysis catheter may be positioned in or close to the atrium of the patient's heart. A low outflow profile tip may be implemented to decrease the outflow velocity of blood being infused through the catheter such that the outflow of blood from the catheter does not cause significant disruption on the vortex flow that naturally occurs within the atrium of the heart. By minimizing the disruption on the vortex flow in the atrium, one may decrease the mixing of newly infused blood with the existing venous blood (i.e., "dirty blood"), thus reducing the recirculation of the processed blood being infused by the catheter.

It has also been observed that a large flow velocity differential, between the velocity of the out flowing infused blood and the velocity of the natural blood flow in the vessel, may promote the formation of thrombosis at the distal tip of the catheter. By reducing the velocity of the blood flowing out of the catheter, the flow velocity differential between the natural and infused flow may be decreased, and this may decrease the thrombus formation at the distal tip of the catheter. Furthermore, the shape of the catheter tip may be configured to create a uniform flow velocity across the entire cross-section directly distal to the catheter tip. Having multiple branching with increasing lumen cross-section within the catheter tip, the outflow of fluids may be dispersed into a larger cross-sectional flow and thus decrease the flow velocity. It may be desirable to control the dispersion such that a uniform flow velocity may be achieved directly distal to the catheter tip. Preferably, the dispersion is wide enough to provide sufficient reduction in overall flow velocity, but not too wide as to create a dead spot at the nose of the bullet shaped catheter tip.

In addition, the aspiration lumen opening of the dual lumen hemodialysis catheter may also be configured in a radial-pattern having a cross-sectional area equal or greater than the proximal portion of the aspiration lumen. This design may reduce the peak velocities of the blood flow as it enters the catheter. One of ordinary skill in the art would appreciate that the "dirty blood" flowing down the major axis of the catheter must reverse direction as it enters the aspiration lumen of the catheter. This tends to cause high shear stress around the fluid entry point. In a traditional "staggered dual-D" design catheter, this high stress at the fluid entry point may lead to the formation of thrombosis. The thrombus formation may result in the occlusion of the lumen opening and reducing the effective life of the catheter. However, with a radial-pattern design and increased cross-sectional area at the aspiration lumen openings, one may reduced the peak velocities as the blood changes direction and enters the catheter. By decreasing the peak inflow velocity, one may decrease the likelihood of thrombus formation at the fluid entry point. Furthermore, a design having greater cross-sectional areas and/or multiple openings for the aspiration lumen may accommodate the occasion when the catheter comes into contact with the vessel/atrium wall and one or several openings are blocked. One of ordinary skilled in the art, having the benefit of the disclosure herein, will appreciate that the number, shape (e.g., tapered shaped, etc.), and size (e.g., length of the opening, etc.) of the lumen openings can be configured to achieve the desired maximum flow velocity and/or fluid shear stress.

Methods for decreasing recirculation, and devices for implementing such methods are also disclosed. In one variation, a dual lumen hemodialysis catheter having two flow ports staggered along the length of the catheter is configured such that the distance between the inflow port and the outflow port is increased to prevent blood being infused through the outflow port being recaptured by the suction at the inflow port. Each of the ports may comprise of one or more orifice. Various tip configurations or orifice structures may be implemented at each of the ports to provide the desired fluid flow profile. Placement of the inflow and outflow ports at specific locations within the circulatory system to reduce recirculation of the blood is also contemplated. Variations of the device disclosed herein may be implemented in medical applications where catheter with low outflow profile is desirable. In some applications, one may design a catheter with a specific outflow profile that meets the needs of a particular medical application. Various design features described herein may also be implemented in a multi-lumen catheter to reduce recirculation of fluid being infused by the catheter.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

As seen in FIG. 2A, "D" depicts the distance between the distal ports (at the tip of the catheter) and the proximal ports.

DETAILED DESCRIPTION OF THE INVENTION

The following detailed description should be read with reference to the drawings, in which like elements in different drawings are identically numbered. The drawings, which are not necessarily to scale, depict selected preferred embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Before describing the present invention, it is to be understood that unless otherwise indicated this invention need not be limited to applications in human. As one of ordinary skill in the art would appreciate, variation of the invention may be applied to other mammals as well. Moreover, while a dual lumen hemodialysis catheter is used herein as an example application to illustrate the functionality of the different aspects of the invention disclosed herein, it should be understood that embodiments of the present invention may be applied to a variety of catheters, including catheters having a single lumen, and catheters having two or more lumens. In addition, the invention may be adapted for connection to the distal end of a catheter to change the outflow profile of the catheter. It must also be noted that, as used in this specification and the appended claims, the singular forms "a," "an" and "the" include plural referents unless the context clearly dictates otherwise. Thus, for example, the term "a lumen" is intended to mean a single lumen or a combination of lumens, "a liquid" is intended to mean one or more liquids, or a mixture thereof.

In one aspect of the invention, the catheter tip is designed to reduce the fluid outflow velocity at the catheter tip relative to the fluid flow velocity inside the lumen along the length of the catheter. In one variation, the catheter is designed with a larger total cross-sectional flow at the catheter tip relative to the cross-sectional flow of the lumen along the length of the catheter. This may be achieved by increasing the diameter of the catheter (thus, increasing the cross-sectional area of the catheter lumen) near the distal tip from which the fluids exit the catheter. Alternatively, the opening for fluid outflow may be increased, or side holes may be added around the distal end of the catheter. In yet another variation, the design combines the features of increasing cross-sectional area of the lumen at the distal portion of the catheter and adding side holes near the distal tip of the catheter.

In another aspect, a catheter tip is designed to reduce the momentum of the outflow fluid in the axial direction distal to the tip of the catheter. In one variation, at least part of the outflow fluid is directed at an angle away from the axial direction. A bullet shaped nose, or a spherical or elliptical profiled tip, may be provided at the distal end of the catheter. Side holes may be incorporated into the curved or angled profile along the tip of the nose. One or more of the angled side holes may direct all or part of the outflow fluid to flow in a direction away form the axial direction distal to the catheter tip. In one example, a plurality of side holes are provided in a radial fashion around the profiled tip at the distal end of the catheter. In another variation, an axial opening at the distal end of the catheter is provided along with the side holes for fluid outflow. In yet another variation, the distal tip is configured without the axial opening and a plurality of angled side holes is provided to direct the outflow of fluids in multiple directions which are angled relative to the central axis along the length of the catheter.

Figure 1A:
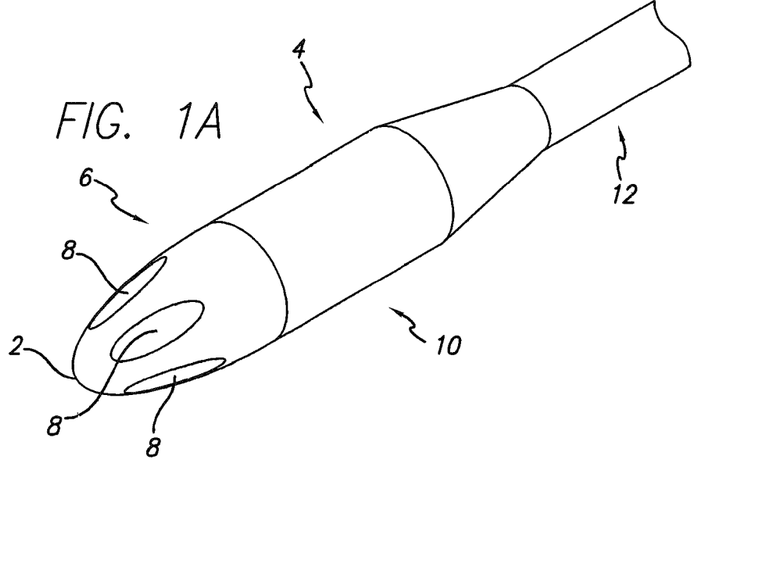
FIG. 1A is an isometric view of one variation of a catheter with a tip configured to reduce the outflow velocity of fluids flowing through the catheter. The distal portion of the catheter is shown.

In one example, the distal end 2 of the catheter 4 is designed with a bullet nose having a radial array of openings 8 angled to intersect with the center lumen of the catheter as shown in the view of FIG. 1A. In this variation, the distal section 10 of the catheter 4, as shown, has a diameter in the range of approximately 3 to 7 mm, and the proximal section 12 of the catheter has a diameter in the range of approximately 2 to 6 mm, although it should be appreciated that a wide range of diameters would be within the scope of the present invention. In a preferred embodiment the proximal section 12 of the catheter is approximately 4 mm and the distal section 10 is approximately 4.5 mm. The catheter tip 6 may be configured such that the combined cross-sectional area of the openings 8 is larger than the cross-sectional area of the center lumen of the catheter 4. As seen in FIG. 1A, the distal section 10 of the catheter 4 has a larger diameter than the proximal section of the catheter 4. However, one of ordinary skill in the art would appreciate that the catheter 4 may also be constructed to have the same diameter between the distal 10 and the proximal 12 sections. For example, one may increase the diameter of the catheter at the proximal section 12 and still maintain the desired functionalities.

Figure 1B:
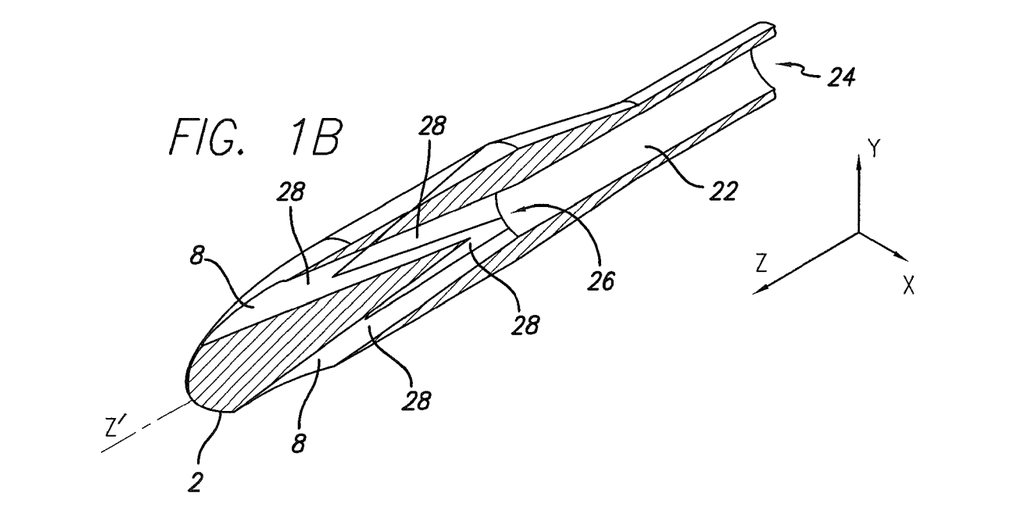
FIG. 1B shows the isometric view of the catheter from FIG. 1A sectioned through the lumen of one of the openings.

FIG. 1B is an isometric view of the catheter tip 6 sectioned through the lumen of one of the openings 8. As seen in FIG. 1B, a primary channel 22 is provided to direct fluid flow from the proximal end 24 of the catheter to the distal end 2 of the catheter. A fluid may be injected into the proximal end 24 of the primary channel 22 and forced to flow toward the distal end 26 of the primary channel 22. At the distal end 26 of the primary channel 22, the fluid is diverted into a plurality of secondary channels 28 that branch from the primary channel 22. The fluid thus is directed to flow in multiple directions. The angle of the secondary channels 28 relative to the central axis of the catheter may be adjusted during the design process to divert the flow in the desired directions. In this design variation, none of the secondary channels are aligned with the central axis of the catheter Z', as shown in FIG. 1B. However, in another variation, one of the secondary channels 28 may extend distally from the primary channel 22 such that it is aligned with the central axis Z' along the length of the catheter.

Figure 1C:
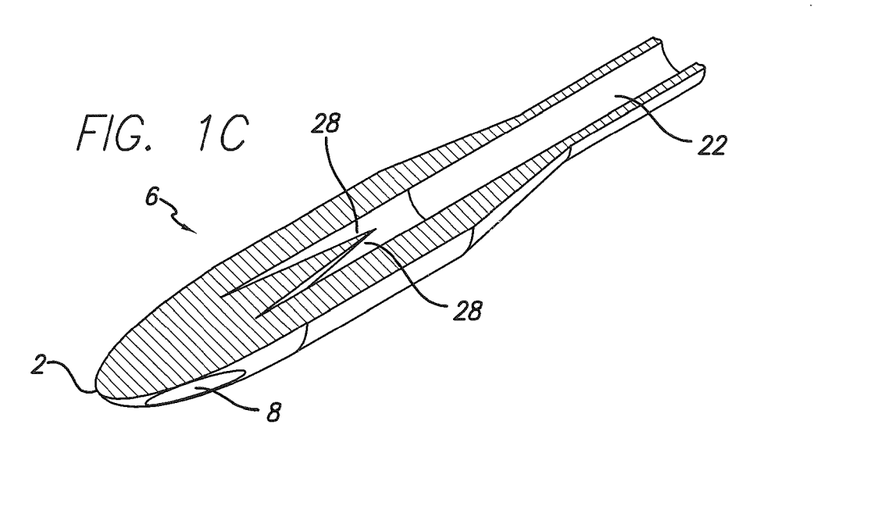
FIG. 1C shows the isometric view of the catheter from FIG. 1A sectioned between the lumen openings.
Figure 1D:
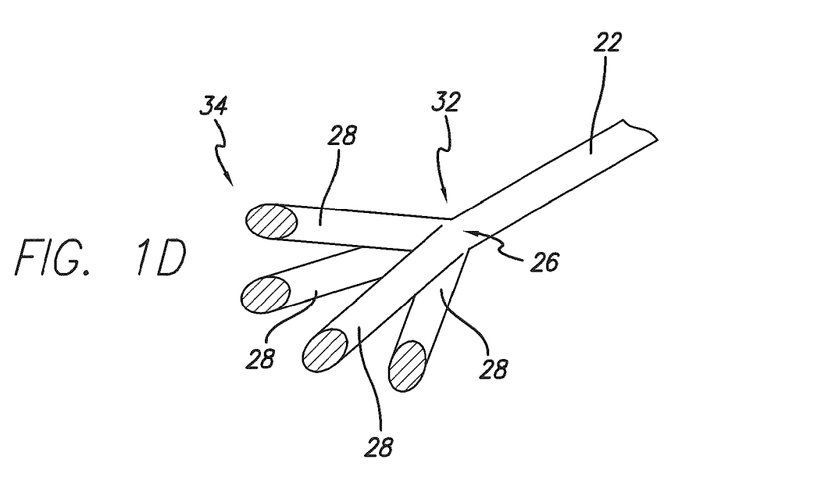
FIG. 1D illustrates one variation of a lumen configuration where a plurality of secondary channels branches off a primary channel forming a larger cross-sectional flow area along the length of the channels after the bifurcation.

FIG. 1C shows the isometric view of the catheter tip 6 sectioned between the lumen openings. FIG. 1D illustrates one possible configuration of primary 22 and secondary 28 channels. In this configuration, four secondary channels 28 branch from the distal end 26 of the primary channel 22. Preferably, each of the secondary channels 28 has a smaller diameter at the proximal end 32 than the distal end 34. Thus, the cross-sectional area within each secondary channel is progressively larger from the proximal end 32 towards the distal end 34. As seen in FIG. 1D, the combined cross-sectional area of the four secondary channels 28 at the distal end 34 is larger than the cross-sectional area of the primary channel 22. Although in this example, the four secondary channels 28 are the same size, one of ordinary skill in the art would appreciate that a catheter with a plurality of secondary channels having varying diameters may be also constructed.

In other variations, the catheter tip may be configured with two, three, four, or more openings for fluid outflow depending on design needs, as one of ordinary skill in the art would appreciate in light of the present disclosure. In other variations, the tip of the catheter may have an overall profile that is circular, polygonal, or elliptical based, or may have a generally hemispherical or semispherical shape. Other shapes or geometries that tend to promote laminar flow at the distal end of the catheter may also be implemented as the catheter tip. In addition, one may construct a catheter having 2, 3, 4, or more secondary channels.

Figure 2A:
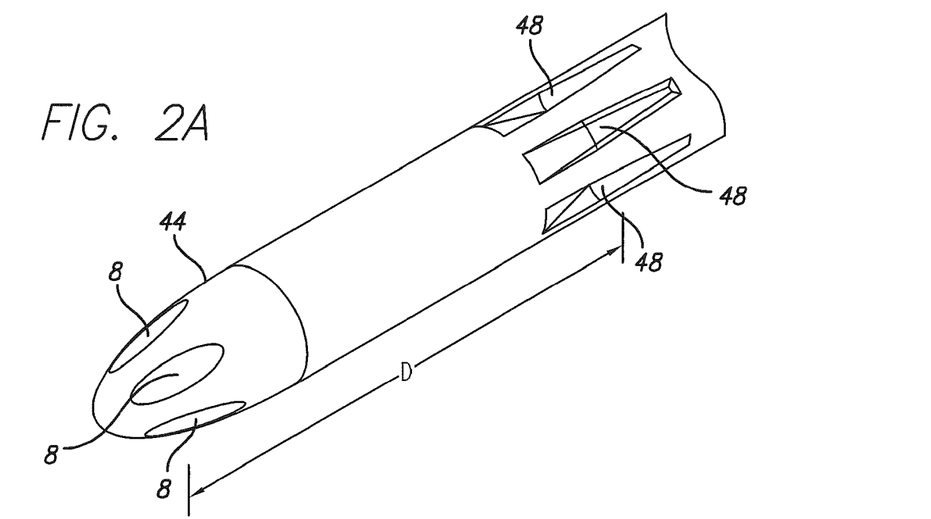
FIG. 2A is an isometric view of one variation of a dual lumen catheter with lumens and ports configured to reduce the outflow velocity of fluids flowing through the catheter. The distal portion of the catheter is shown.
Figure 2B:
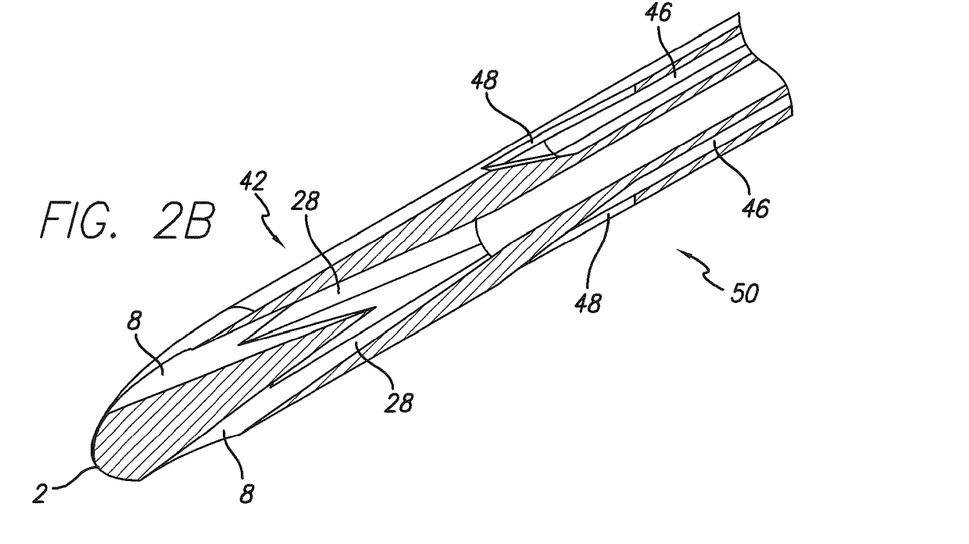
FIG. 2B shows the isometric view of the catheter from FIG. 2A sectioned through the lumen of one of the openings.
Figure 2C:
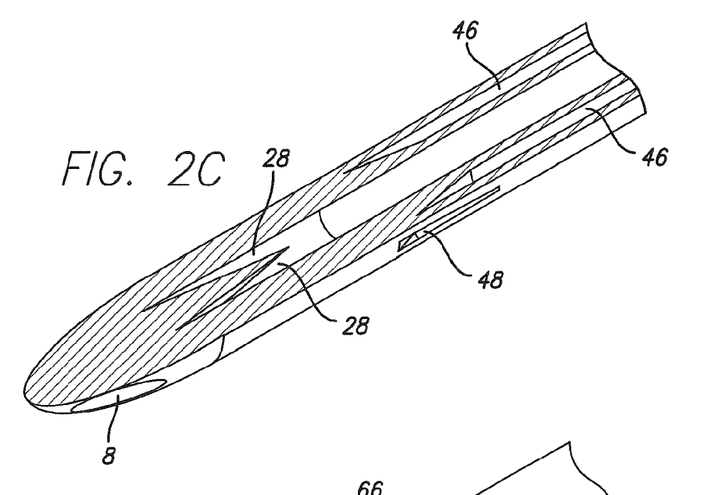
FIG. 2C shows the isometric view of the catheter from FIG. 2A sectioned between the lumen openings.

In another variation, the bullet shaped tip and radial openings 8 are implemented in a dual lumen catheter 42 having a co-axial lumen design, as shown in FIG. 2A. In this variation the catheter has a diameter in the range of approximately 3 to 7 mm, although again, it should be appreciated that a wide range of diameters would be within the scope of the present invention. The bullet nose 44 has a radial array of openings 8 angled to intersect with the center (i.e., inner) lumen 22 of the catheter. The catheter tip may be configured such that the combined cross-sectional area of the openings 8 is larger than the cross-sectional area of the center lumen 22 of the catheter 42. The annular (i.e., outer) lumen 46 of the catheter terminates in a radial array of tapered slots 48 on outer circumference at the distal portion 50 of the catheter. The tapered slots 48 may be configured such that the cumulative cross-sectional area of the slots 48 is greater than the cross-sectional area of the annular lumen 46. FIG. 2B is an isometric view of the dual lumen catheter 42 sectioned through the lumen of one of the openings 8. FIG. 2C is an isometric view of the dual lumen catheter 42 sectioned between the lumen openings 8. Similar to the single lumen catheter design, the dual lumen catheter design may be configured with various number of openings. Various shapes and geometries that tend to promote laminar flow at the distal end of the catheter may also be implemented. The openings to the annular lumen may be configured with various shapes and varying in numbers.

The radial array of openings at the tip of the catheter may serve to reduce exit velocity of fluid around the catheter tip relative to the flow velocity at the inner lumen of the catheter. In one variation, the catheter tip is designed to reduce the exit velocity by 25% or more relative to the velocity inside the primary catheter lumen. In another variation, the catheter tip is designed to reduce the exit velocity by 50% or more relative to the velocity inside the primary catheter lumen. In yet another variation, the catheter tip is designed to reduce the exit velocity by 75% or more relative to the velocity inside the primary catheter lumen. For hemodialysis catheter application where the tip of the catheter is intended to be placed either inside the right atrium or within the superior vena cava, preferably, the catheter is configured such that the exit velocity around the catheter tip is reduced to approximately 50 inches per second or less; more preferably the catheter is configured such that the exit velocity around the catheter tip is reduced to approximately 30 inches per second or less; and even more preferably the catheter is configured such that the exit velocity around the catheter tip is reduced to approximately 15 inches per second or less.

As seen in the earlier examples, the radial opening design at the tip of the catheter may be combined with the bullet nose or other profiled nose design to achieve low exit flow velocity and minimize disruption to the laminar flow around the distal end of the catheter. In light of the disclosure herein, one of ordinary skill in the art would appreciate that the size and number of openings may be tailored to create catheters with specific outflow profile matching pre-defined parameters. For example, the shape of the radial openings may be configured to minimize pressure drop of flow rates within each opening. In one variation, tapered shaped slots are utilized in an attempt to equalize the pressure drop along the length of the openings.

When the combined cross-sectional area of the openings, which are connected to a common lumen, is larger than the cross-sectional area of the common lumen, the flow velocity inside the openings may, as a result, be lower than the flow velocity inside the common lumen. Preferably, the combined cross-sectional area of the openings is at least 10% larger than the cross-sectional area of the common catheter lumen; more preferably the combined cross-sectional area of the opening is at least 30% larger than the cross-sectional area of the common catheter lumen; yet more preferably the combined cross-sectional area of the openings is at least 50% larger than the common catheter lumen; even more preferably the combined cross-sectional area of the openings is at least 100% larger than the cross-sectional area of the common catheter lumen. In one variation, both the oval openings at the distal tip, which connect to the inner lumen of a dual lumen catheter, and the slot openings along the length of the catheter, which connect to the outer lumen, are configured such that the combined cross-sectional area of each set of openings is twice the cross-sectional area of their corresponding lumen within the catheter.

Figure 3:
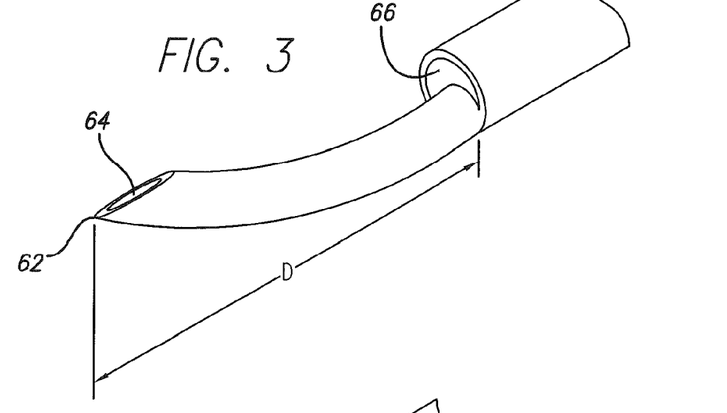
FIG. 3 shows another variation of a dual lumen catheter where the two lumens are positioned side by side and the distal openings of the lumens are staggered along the length of the catheter.
Figures 4, 5:
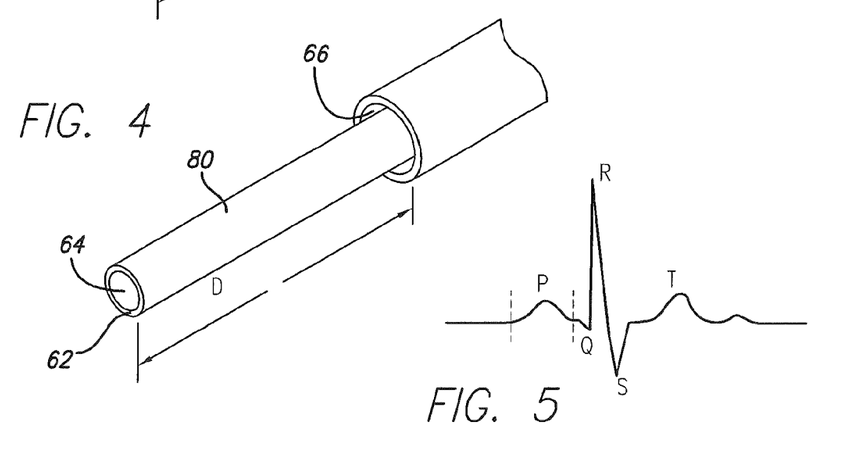
FIG. 4 shows yet another variation of a dual lumen catheter where the two lumens are positioned coaxially and the distal openings of the lumens are located one after the other along the length of the catheter.
FIG. 5 illustrates a typical electrocardiogram of an entire electrical cardiac cycle.

In another variation, a multi-lumen catheter is provided wherein one set of lumens exit at the distal end of the catheter and a second set of lumens exit at an area along the length of the catheter. FIG. 3 illustrates one variation of the multi-lumen catheter comprising two lumens with the first lumen exiting at a distal end 62 at a distal opening 64, and the second lumen staggered on top of the first lumen to exit proximal the distal end 62 at a proximal opening 66. Another variation is shown in FIG. 4, where the dual lumen catheter comprises a coaxial tubing forming an inner lumen and an outer lumen. The inner lumen exits at the distal end 62 of the catheter at the distal opening 64 and the outer lumen exits at a proximal opening 66 located along the length of the inner tubing 80, proximal the distal end 62. These multi lumen catheters may be configured as a hemodialysis catheter with one lumen utilized for removing "dirty blood" from the vein and the second lumen utilized to deliver the processed blood back into circulation.

In one variation, the dual lumen catheter is configured such that when the catheter is positioned within a patient's superior vena cava for hemodialysis, the distal opening of the catheter is positioned within the right atrium of the heart. Preferably, the distal tip of the catheter does not contact the atrioventricular (AV) valve or the wall of the heart, but is positioned in close proximity thereto. At the same time, when the distal tip of the catheter is positioned within the right atrium, the proximal opening of the catheter would be above the atrium. Preferably, the proximal opening is located within the superior vena cava (SVC) or near the SVC/jugular vein junction. A dual lumen catheter so configured may reduce the recirculation of the processed blood being introduced through the distal opening. By increasing the separation between the distal opening and the proximal opening, one may decrease the recirculation of blood since the probability that the proximal opening would capture the blood infused by the distal opening would decrease.

The distance between the distal opening and the proximal opening ("D" as shown in FIGS. 2A, 3 and 4) that allows the proper position of the distal and proximal openings may vary depending on the patient's physical size. Thus, the physician may match the catheter of appropriate size (i.e., having the desired "D" distance) to a patient depending on the patient's physical characteristics. Alternatively, non-invasive imaging techniques such as X-ray or MRI may be used to determine the proper size of dialysis catheter to implant inside the patient. Optionally, one may design a dual lumen catheter where the distance "D" between the distal opening and the proximal opening is large enough such that when it is implanted inside an average adult the proximal opening will be inside the SVC when the distal opening is placed inside the right atrium of the patient. Preferably, D for an average adult would be between approximately 25 and 50 mm.

As discussed above, before implantation of a dialysis catheter, the physician may determine the proper size of catheter to use depending on the physical size and/or weight of the patient. In addition, non-invasive imaging techniques may also be applied to assist the physician in making such a determination. In one example, the catheter is inserted into the right internal jugular vein. The catheter is then advanced into the patient's body along the internal jugular vein. Further advancement will push the distal section of the catheter into the superior vena cava, and then into the right atrium. Ultrasound, fluoroscopy, radiography, and/or other imaging methods may be utilized to assist the physician in the placement of the catheter. A radiopaque ribbon may be provided at the distal end of the catheter and/or along the length of the catheter to improve contrast of the catheter within the images captured by the imaging device.

Once the tip of the catheter enters the right atrium, the physician can adjust the position of the catheter. Preferably, the distal tip is positioned in close proximity (within the range of approximately 1-6 cm) to the AV valve (i.e., the tricuspid valve) but does not come into contact with the AV valve or the wall of the right atrium. In one variation, when the distal tip of the catheter is placed within the atrium, the proximal opening of the catheter will be located within the SVC. In another variation, when the distal tip of the catheter is placed within the atrium, the proximal opening will be located within the upper portion of the SVC. In yet another variation, when the distal tip of the catheter is place within the atrium, the proximal opening will be located in close proximity (within the range of approximately 1-6 cm) to the SVC/jugular vein junction. Once the catheter is placed in the desired position, the physician may then secure the catheter in place. Optionally, the proximal end of the catheter may be tunneled underneath the skin so that it exits the skin just beneath the right clavicle and distant from the insertion site. When the catheter has been satisfactorily placed, a hemodialysis machine may be connected to the proximal end of the catheter to begin the dialyses process. Blood may be removed through suction delivered through the catheter to the proximal opening of the catheter which is located within the SVC, and processed blood may be infused into the atrium through the distal opening on the catheter.

Although in the above examples, each of the distal and proximal openings comprises a single opening, one of ordinary skill in the art would appreciate that each of the distal and proximal openings may comprise a plurality of orifices. For example, the catheter shown in FIG. 2A may also be implemented in the above described procedure. In addition, features and components discussed earlier for reducing exit flow velocity around the catheter tip and for reducing outflow momentum in the axial direction of the catheter may also be implemented in combination with the multi-lumen catheters having specific distance, 'D', between the distal opening and the proximal opening. By reducing the exit velocity of outflow blood at the distal opening, one may reduce the likelihood that the outflow blood is recaptured by the suction at the proximal opening. By directing the outflow at the distal opening in various directions, one may minimize the disruption of the infused blood on the natural vortex that occurs inside the right atrium, which in turn may minimize mixing of the infused blood with arterial blood and thus decreases recirculation. In yet another variation, the distal opening is configured such that the opening directs the outflow of the infused blood into the AV valve. As a result, when the AV valve is open the bulk of the fluid exiting the distal opening of the catheter may flow into the right ventricle of the heart.

In another aspect, the infused blood is modulated with respect to the cardiac cycle. This delivery approach may improve the efficiency of fluid delivery and may further minimize the amount of recirculation in the hemodialysis catheter. In one variation, the infusion of blood through the distal opening of the hemodialysis catheter is synchronized with the filling and emptying of the right atrium. In one example, a controller monitors the signal from the sinoatrial (SA) node and opens a solenoid pinch clamp as the atrium empties. In another example, a computer controller monitors the electrocardiogram (EKG) and controls a solenoid valve to open and close based on the heart beat cycle represented by the EKG signal. The solenoid valve or clamp controls the infusion of blood into the hemodialysis catheter. As one of ordinary skilled in the art would appreciate, variations of valves, clamp, controller and EKG monitors may be configured to control the infusion of blood flow into the implanted catheter.

The SA node initiates the cardiac cycle. When the atrium is depolarizing, it transmits a P-wave in the EKG cardiac cycle, shown in FIG. 5. Next, the SA node causes a transmission delay of the electrical energy, which provides the ventricle time to fill. Therefore, if the solenoid pinch valve is timed so that it opens just after the P-wave, it may allow the infused blood from the catheter to flow into the atrium as the AV valve (i.e., tricuspid valve) opens. In one variation, the solenoid valve is open during the P-wave period and closed during the rest of the heart cycle. In another variation, the solenoid valve is completely open during the P-wave period to allow maximum infusion of the blood, and the solenoid valve is only partially open during the rest of the heart cycle to allow slow infusion of the blood inside the right atrium while the AV valve is closed.

In yet another variation, the P-wave is used to modulate the pump inside the dialysis machine. An EKG monitor provides the feedback to the computer controller that controls the rate of operation of the pump inside the dialysis machine. The controller may increase the pump rate during the P-wave period and decrease the pump rate when the EKG is outside of the P-wave period. Alternatively, the rate of the pump may be set to increase at a defined time prior to the projected occurrence of the P-wave and start to decrease once the Q-wave is detected. In another variation, the pump is modulated to increase and decrease output of the dialysis instrument based of signal processing and/or modeling of the detected EKG to optimize the hemodialysis process. By changing the flow rate of the blood passing through the dialysis system, one may be able to improve the efficiency of the dialysis process since the blood moving through the dialysis membrane is stalled or slowed for a period of time during the cardiac cycle, and this may allow more waste particles in the blood to diffuse through the membrane and increase the efficiency of the dialysis machine in removing waste particles from the blood.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A method of performing a hemodialysis procedure, comprising:
   providing a catheter including:
      a primary channel extending along a primary portion from a proximal end of the catheter to a distal section of the catheter, the primary portion having a first outer diameter;
      a plurality of secondary channels branching from a terminal end of the primary channel in the distal section, each of the plurality of secondary channels in fluid communication with one of a plurality of openings in the distal section, the distal section having a second outer diameter greater than the first outer diameter;

infusing a fluid through the primary channel;

reducing the velocity of the fluid in the distal section when the fluid moves through the secondary channels; and directing the fluid through the plurality of openings such that the fluid exits the catheter in different directions away from the distal section of the catheter.

2. The method according to claim 1, wherein the fluid is at least partially directed into a right atrium of the patient.

3. The method according to claim 1, further comprising withdrawing blood from a superior vena cava of the patient while the fluid is directed into the fight atrium of the patient.

4. The method according to claim 1, wherein the catheter further includes a bullet nose.

5. The method according to claim 1, wherein the plurality of openings comprise a radial array of openings around a circumference of the catheter.

6. The method according to claim 1, wherein a combined cross-sectional area of the plurality of openings is larger than a cross-sectional area of the primary channel.

7. The method according to claim 1, wherein a distal end of the catheter has a third diameter, and wherein the second diameter is greater than the third diameter.

8. The method according to claim 1, wherein each of the secondary channels has a proximal cross-sectional diameter adjacent the primary channel smaller than a distal cross-sectional diameter.

9. The method according to claim 8, wherein a combined cross-sectional area of the secondary channels distal cross-sectional diameter is larger than a cross-sectional area of the primary channel.

10. The method according to claim 1, wherein the plurality of openings are circumferentially aligned.

* * * * *